(12) United States Patent
Ferree

(10) Patent No.: US 8,038,713 B2
(45) Date of Patent: Oct. 18, 2011

(54) TWO-COMPONENT ARTIFICIAL DISC REPLACEMENTS

(75) Inventor: Bret A. Ferree, Cincinnati, OH (US)

(73) Assignee: SpineCore, Inc., Allendale, NJ (US)

( * ) Notice: Subject to any disclaimer, the term of this patent is extended or adjusted under 35 U.S.C. 154(b) by 0 days.

(21) Appl. No.: 10/421,304

(22) Filed: Apr. 23, 2003

(65) Prior Publication Data

US 2004/0073311 A1    Apr. 15, 2004

Related U.S. Application Data

(63) Continuation-in-part of application No. 10/413,028, filed on Apr. 14, 2003.

(60) Provisional application No. 60/374,747, filed on Apr. 23, 2002.

(51) Int. Cl.
*A61F 2/44* (2006.01)
(52) U.S. Cl. ...................................... 623/17.11
(58) Field of Classification Search ............... 623/16.11, 623/17.11–17.16, 18.11; 606/61
See application file for complete search history.

(56) References Cited

U.S. PATENT DOCUMENTS

| | | | |
|---|---|---|---|
| 3,278,107 A | 10/1966 | Rygg | |
| 3,486,505 A | 12/1969 | Morrison | |
| 3,872,519 A | 3/1975 | Giannestras et al. | |
| 4,021,864 A | 5/1977 | Waugh | |
| 4,105,407 A | 8/1978 | Sanderson | |
| 4,457,484 A | 7/1984 | Hameister | |
| 4,528,980 A | 7/1985 | Kenna | |
| 4,759,766 A * | 7/1988 | Buettner-Janz et al. | ... 623/17.15 |
| 4,759,769 A | 7/1988 | Hedman et al. | |
| 4,917,704 A | 4/1990 | Frey et al. | |
| 4,955,908 A | 9/1990 | Frey et al. | |
| 4,997,432 A | 3/1991 | Keller | |
| 5,002,576 A | 3/1991 | Fuhrmann et al. | |
| 5,030,219 A | 7/1991 | Matsen, III et al. | |
| 5,122,130 A | 6/1992 | Keller | |
| 5,236,460 A | 8/1993 | Barber | |
| 5,258,031 A | 11/1993 | Salib et al. | |
| 5,314,477 A | 5/1994 | Marnay | |
| 5,370,697 A | 12/1994 | Baumgartner et al. | |

(Continued)

FOREIGN PATENT DOCUMENTS

FR    2 718 635 A1    10/1995

(Continued)

*Primary Examiner* — Eduardo C Robert
*Assistant Examiner* — David Comstock
(74) *Attorney, Agent, or Firm* — Lerner, David, Littenberg, Krumholz & Mentlik, LLP

(57) ABSTRACT

Artificial disc replacements (ADRs) and total disc replacements (TDRs) are based upon two, directly articulating components, resulting in a restricted-motion system that better approximates more normal spinal flexion, extension, and lateral bending. One component has a concave articulating surface, and the other with a convex articulating surface. The radius of curvature of the articulating surface is smaller in the anterior to posterior direction of the ADR than radius of curvature of the articulating surface in the left to right direction of the ADR. The use of an articulating surface with two or more radius of curvature also limits axial rotation, thereby protecting the facet joints and the Annulus Fibrosus (AF). The two different radii used to create the articulating surfaces also naturally leads to an oval shape as seen from the top, which better fits the oval shape of the vertebral endplate better than circularly shaped ADRs. Both components are preferably made of a hard material and are highly polished to reduce friction.

20 Claims, 19 Drawing Sheets

U.S. PATENT DOCUMENTS

| | | | |
|---|---|---|---|
| 5,401,269 A * | 3/1995 | Buttner-Janz et al. | 623/17.15 |
| 5,405,400 A | 4/1995 | Linscheid et al. | |
| 5,425,773 A * | 6/1995 | Boyd et al. | 623/17.15 |
| 5,458,641 A | 10/1995 | Ramirez Jimenez | |
| 5,507,816 A | 4/1996 | Bullivant | |
| 5,514,180 A | 5/1996 | Heggeness et al. | |
| 5,522,900 A | 6/1996 | Hollister | |
| 5,534,029 A | 7/1996 | Shima | |
| 5,549,690 A | 8/1996 | Hollister et al. | |
| 5,556,431 A | 9/1996 | Buttner-Janz | |
| 5,556,432 A * | 9/1996 | Kubein-Meesenburg et al. | 623/20.21 |
| 5,562,738 A | 10/1996 | Boyd et al. | |
| 5,599,279 A | 2/1997 | Slotman et al. | |
| 5,645,605 A | 7/1997 | Klawitter | |
| 5,653,762 A | 8/1997 | Pisharodi | |
| 5,674,296 A | 10/1997 | Bryan et al. | |
| 5,676,701 A | 10/1997 | Yuan et al. | |
| 5,683,464 A | 11/1997 | Wagner et al. | |
| 5,683,465 A | 11/1997 | Shinn et al. | |
| 5,720,751 A | 2/1998 | Jackson | |
| 5,733,290 A | 3/1998 | McCue et al. | |
| 5,755,796 A | 5/1998 | Ibo et al. | |
| 5,769,856 A | 6/1998 | Dong et al. | |
| 5,782,830 A | 7/1998 | Farris | |
| 5,782,832 A | 7/1998 | Larsen et al. | |
| 5,865,846 A | 2/1999 | Bryan et al. | |
| 5,888,223 A | 3/1999 | Bray, Jr. | |
| 5,888,226 A | 3/1999 | Rogozinski | |
| 5,893,889 A | 4/1999 | Harrington | |
| 5,895,428 A | 4/1999 | Berry | |
| 5,899,941 A | 5/1999 | Nishijima et al. | |
| 5,916,267 A | 6/1999 | Tienboon | |
| 5,928,284 A | 7/1999 | Mehdizadeh | |
| 5,989,291 A | 11/1999 | Ralph et al. | |
| 6,001,130 A | 12/1999 | Bryan et al. | |
| 6,019,792 A | 2/2000 | Cauthen | |
| 6,039,763 A * | 3/2000 | Shelokov | 623/17.16 |
| 6,051,751 A | 4/2000 | Sioshansi et al. | |
| 6,063,121 A | 5/2000 | Xavier et al. | |
| 6,066,174 A | 5/2000 | Farris | |
| 6,066,175 A | 5/2000 | Henderson et al. | |
| 6,093,205 A | 7/2000 | McLeod et al. | |
| 6,093,207 A | 7/2000 | Pisharodi | |
| 6,096,080 A | 8/2000 | Nicholson et al. | |
| 6,106,557 A | 8/2000 | Robioneck et al. | |
| 6,113,602 A | 9/2000 | Sand | |
| 6,113,637 A | 9/2000 | Gill et al. | |
| 6,113,638 A | 9/2000 | Williams et al. | |
| 6,139,550 A | 10/2000 | Michaelson | |
| 6,143,012 A | 11/2000 | Gausepohl et al. | |
| 6,146,421 A * | 11/2000 | Gordon et al. | 623/17.15 |
| 6,156,067 A | 12/2000 | Bryan et al. | |
| 6,159,215 A | 12/2000 | Urbahns et al. | |
| 6,174,311 B1 | 1/2001 | Branch et al. | |
| 6,179,873 B1 | 1/2001 | Zientek | |
| 6,179,874 B1 | 1/2001 | Cauthen | |
| 6,190,413 B1 | 2/2001 | Sutcliffe | |
| 6,193,757 B1 | 2/2001 | Foley et al. | |
| 6,213,055 B1 | 4/2001 | Willinger et al. | |
| 6,214,005 B1 | 4/2001 | Benzel et al. | |
| 6,217,615 B1 | 4/2001 | Sioshansi et al. | |
| 6,224,607 B1 | 5/2001 | Michelson | |
| 6,228,118 B1 | 5/2001 | Gordon | |
| 6,235,034 B1 | 5/2001 | Bray | |
| 6,235,060 B1 * | 5/2001 | Kubein-Meesenburg et al. | 623/20.31 |
| 6,241,769 B1 | 6/2001 | Nicholson et al. | |
| 6,277,149 B1 | 8/2001 | Boyle et al. | |
| 6,296,647 B1 | 10/2001 | Robioneck et al. | |
| 6,319,257 B1 | 11/2001 | Carignan et al. | |
| 6,325,828 B1 * | 12/2001 | Dennis et al. | 623/20.14 |
| 6,342,057 B1 | 1/2002 | Brace et al. | |
| 6,368,350 B1 | 4/2002 | Erickson et al. | |
| 6,395,030 B1 | 5/2002 | Songer et al. | |
| 6,395,032 B1 | 5/2002 | Gauchet | |
| 6,398,815 B1 | 6/2002 | Pope et al. | |
| 6,413,259 B1 | 7/2002 | Lyons et al. | |
| 6,416,551 B1 | 7/2002 | Keller | |
| 6,428,544 B1 | 8/2002 | Ralph et al. | |
| 6,432,106 B1 | 8/2002 | Fraser | |
| 6,436,102 B1 | 8/2002 | Ralph et al. | |
| 6,440,168 B1 | 8/2002 | Cauthen | |
| 6,461,359 B1 | 10/2002 | Tribus et al. | |
| 6,468,310 B1 | 10/2002 | Ralph et al. | |
| 6,471,725 B1 | 10/2002 | Ralph et al. | |
| 6,478,796 B2 | 11/2002 | Zucherman et al. | |
| 6,478,800 B1 | 11/2002 | Fraser et al. | |
| 6,517,580 B1 | 2/2003 | Ramadan et al. | |
| 6,524,312 B2 | 2/2003 | Landry et al. | |
| 6,527,804 B1 | 3/2003 | Gauchet et al. | |
| 6,540,785 B1 | 4/2003 | Gill et al. | |
| 6,562,073 B2 | 5/2003 | Foley | |
| 6,576,017 B2 | 6/2003 | Foley et al. | |
| 6,579,290 B1 | 6/2003 | Hardcastle et al. | |
| 6,579,320 B1 | 6/2003 | Gauchet et al. | |
| 6,579,321 B1 | 6/2003 | Gordon et al. | |
| 6,582,466 B1 | 6/2003 | Gauchet et al. | |
| 6,582,468 B1 | 6/2003 | Gauchet et al. | |
| 6,589,247 B2 | 7/2003 | McGahan et al. | |
| 6,602,292 B2 | 8/2003 | Burkinshaw | |
| 6,610,093 B1 | 8/2003 | Pisharodi | |
| 6,645,248 B2 * | 11/2003 | Casutt | 623/17.12 |
| 6,652,525 B1 | 11/2003 | Assaker et al. | |
| 6,652,533 B2 | 11/2003 | O'neil | |
| 6,666,866 B2 | 12/2003 | Martz et al. | |
| 6,679,887 B2 | 1/2004 | Nicholson et al. | |
| 6,679,915 B1 | 1/2004 | Cauthen | |
| 6,682,562 B2 | 1/2004 | Viart et al. | |
| 6,706,068 B2 | 3/2004 | Ferree | |
| 6,716,245 B2 | 4/2004 | Pasquet et al. | |
| 6,740,118 B2 | 5/2004 | Eisermann et al. | |
| 6,743,257 B2 | 6/2004 | Castro | |
| 6,793,678 B2 | 9/2004 | Hawkins | |
| 6,800,093 B2 | 10/2004 | Nicholson et al. | |
| 6,835,206 B2 | 12/2004 | Jackson | |
| 6,837,905 B1 | 1/2005 | Lieberman | |
| 6,896,676 B2 | 5/2005 | Zubok et al. | |
| 6,908,484 B2 | 6/2005 | Zubok et al. | |
| 6,936,071 B1 | 8/2005 | Marnay et al. | |
| 6,972,037 B2 | 12/2005 | Zubok et al. | |
| 6,972,038 B2 | 12/2005 | Zubok et al. | |
| 6,981,990 B2 | 1/2006 | Keller et al. | |
| 6,986,789 B2 | 1/2006 | Schultz et al. | |
| 6,991,654 B2 | 1/2006 | Foley | |
| 6,994,727 B2 | 2/2006 | Khandkar et al. | |
| 6,994,728 B2 | 2/2006 | Zubok et al. | |
| 6,994,729 B2 | 2/2006 | Zubok et al. | |
| 6,997,954 B2 | 2/2006 | Zubok et al. | |
| 6,997,955 B2 | 2/2006 | Zubok et al. | |
| 7,022,139 B2 | 4/2006 | Errico et al. | |
| 7,056,344 B2 | 6/2006 | Huppert et al. | |
| 7,063,725 B2 | 6/2006 | Foley | |
| 7,125,425 B2 | 10/2006 | Foley et al. | |
| 7,198,643 B2 | 4/2007 | Zubok et al. | |
| 7,204,852 B2 | 4/2007 | Marnay et al. | |
| 7,226,452 B2 | 6/2007 | Zubok et al. | |
| 7,235,104 B2 | 6/2007 | Grinberg et al. | |
| 7,270,679 B2 | 9/2007 | Istephanous et al. | |
| 7,300,441 B2 | 11/2007 | Haid et al. | |
| 7,320,689 B2 | 1/2008 | Keller | |
| 2001/0005796 A1 | 6/2001 | Zdeblick et al. | |
| 2001/0007073 A1 | 7/2001 | Zucherman et al. | |
| 2001/0010001 A1 | 7/2001 | Michelson | |
| 2001/0012938 A1 | 8/2001 | Zucherman et al. | |
| 2001/0020170 A1 | 9/2001 | Zucherman et al. | |
| 2001/0027343 A1 | 10/2001 | Keller | |
| 2002/0004683 A1 | 1/2002 | Michelson | |
| 2002/0017789 A1 | 2/2002 | Holmes et al. | |
| 2002/0035400 A1 | 3/2002 | Bryan et al. | |
| 2002/0082597 A1 | 6/2002 | Fraser | |
| 2002/0082701 A1 | 6/2002 | Zdedblick et al. | |
| 2002/0107571 A1 | 8/2002 | Foley | |
| 2002/0107572 A1 | 8/2002 | Foley et al. | |
| 2002/0123750 A1 | 9/2002 | Eisermann et al. | |
| 2002/0128715 A1 | 9/2002 | Bryan et al. | |

| | | | | | | |
|---|---|---|---|---|---|---|
| 2002/0143399 A1 | 10/2002 | Sutcliffe | | 2004/0193272 A1 | 9/2004 | Zubok et al. |
| 2002/0147450 A1 | 10/2002 | LeHuec et al. | | 2004/0215198 A1 | 10/2004 | Marnay et al. |
| 2002/0169508 A1 | 11/2002 | Songer et al. | | 2004/0220567 A1 | 11/2004 | Eisermann et al. |
| 2002/0193880 A1 | 12/2002 | Fraser | | 2004/0243240 A1 | 12/2004 | Beaurain et al. |
| 2003/0028197 A1 | 2/2003 | Hanson et al. | | 2004/0267369 A1 | 12/2004 | Lyons et al. |
| 2003/0028249 A1 | 2/2003 | Baccelli et al. | | 2005/0021042 A1 | 1/2005 | Marnay et al. |
| 2003/0040796 A1 | 2/2003 | Ferree | | 2005/0033430 A1 | 2/2005 | Powers et al. |
| 2003/0045939 A1 | 3/2003 | Casutt | | 2005/0043800 A1 | 2/2005 | Paul et al. |
| 2003/0060886 A1 | 3/2003 | Van Hoeck et al. | | 2005/0043803 A1 | 2/2005 | Schultz et al. |
| 2003/0069586 A1 | 4/2003 | Errico et al. | | 2005/0055029 A1 | 3/2005 | Marik et al. |
| 2003/0074064 A1 | 4/2003 | Gerbec et al. | | 2005/0071013 A1 | 3/2005 | Zubok et al. |
| 2003/0078668 A1 | 4/2003 | Michelson | | 2005/0085917 A1 | 4/2005 | Marnay et al. |
| 2003/0093153 A1 | 5/2003 | Banick et al. | | 2005/0143749 A1 | 6/2005 | Zalenski et al. |
| 2003/0100949 A1 | 5/2003 | Michelson | | 2005/0159819 A1 | 7/2005 | McCormack et al. |
| 2003/0109928 A1 | 6/2003 | Pasquet et al. | | 2005/0165487 A1 | 7/2005 | Muhanna et al. |
| 2003/0120344 A1 | 6/2003 | Michelson | | 2005/0197705 A1 | 9/2005 | Arnin et al. |
| 2003/0125748 A1 | 7/2003 | Li et al. | | 2005/0228497 A1 | 10/2005 | Ferree et al. |
| 2003/0135278 A1 | 7/2003 | Eckman | | 2005/0228500 A1 | 10/2005 | Kim et al. |
| 2003/0135279 A1 | 7/2003 | Michelson | | 2005/0240270 A1 | 10/2005 | Zubok et al. |
| 2003/0149482 A1 | 8/2003 | Michelson | | 2005/0240271 A1 | 10/2005 | Zubok et al. |
| 2003/0167091 A1 | 9/2003 | Scharf | | 2005/0240272 A1 | 10/2005 | Zubok et al. |
| 2003/0167092 A1 | 9/2003 | Foley | | 2005/0240273 A1 | 10/2005 | Khandkar et al. |
| 2003/0176921 A1 | 9/2003 | Lawson | | 2005/0256577 A1 | 11/2005 | Baumgartner et al. |
| 2003/0176922 A1 | 9/2003 | Lawson et al. | | 2005/0267581 A1 | 12/2005 | Marnay et al. |
| 2003/0176923 A1 | 9/2003 | Keller et al. | | 2005/0267582 A1 | 12/2005 | Ferree et al. |
| 2003/0181982 A1 | 9/2003 | Kuslich | | 2005/0283237 A1 | 12/2005 | Zucherman et al. |
| 2003/0187454 A1 | 10/2003 | Gill et al. | | 2006/0004377 A1 | 1/2006 | Keller |
| 2003/0191534 A1 | 10/2003 | Viart et al. | | 2006/0030857 A1 | 2/2006 | de Villiers et al. |
| 2003/0195632 A1 | 10/2003 | Foley et al. | | 2006/0036326 A1 | 2/2006 | Baumgartner et al. |
| 2003/0199981 A1 | 10/2003 | Ferree | | 2006/0069439 A1 | 3/2006 | Zucherman et al. |
| 2003/0199983 A1 | 10/2003 | Michelson | | 2006/0085077 A1 | 4/2006 | Cook et al. |
| 2003/0204260 A1 | 10/2003 | Ferree | | 2006/0116768 A1 | 6/2006 | Krueger et al. |
| 2003/0208274 A1 | 11/2003 | Davis | | 2006/0149273 A1 | 7/2006 | Ross et al. |
| 2003/0216744 A1 | 11/2003 | Longhini et al. | | 2006/0167461 A1 | 7/2006 | Hawkins et al. |
| 2003/0216810 A1 | 11/2003 | Ralph et al. | | 2006/0178748 A1 | 8/2006 | Dinger et al. |
| 2003/0229358 A1 | 12/2003 | Errico et al. | | 2006/0217731 A1 | 9/2006 | Gil et al. |
| 2003/0229397 A1 | 12/2003 | Davis | | 2006/0282020 A1 | 12/2006 | Bertagnoli et al. |
| 2003/0233097 A1 | 12/2003 | Ferree | | 2007/0073403 A1 | 3/2007 | Lombardo et al. |
| 2003/0233148 A1 | 12/2003 | Ferree | | 2007/0073405 A1 | 3/2007 | Verhulst et al. |
| 2004/0002759 A1 | 1/2004 | Ferree | | 2007/0106388 A1 | 5/2007 | Michelson |
| 2004/0002761 A1 | 1/2004 | Rogers | | 2007/0112429 A1 | 5/2007 | Muhanna et al. |
| 2004/0002762 A1 | 1/2004 | Hawkins | | 2007/0118224 A1 | 5/2007 | Shah et al. |
| 2004/0006343 A1 | 1/2004 | Sevrain | | 2007/0225813 A1 | 9/2007 | Haines |
| 2004/0010254 A1 | 1/2004 | Cook et al. | | 2007/0265707 A1 | 11/2007 | Marnay et al. |
| 2004/0010316 A1 | 1/2004 | William et al. | | 2007/0282448 A1 | 12/2007 | Abdou |
| 2004/0024459 A1 | 2/2004 | Ferree | | 2008/0033563 A1 | 2/2008 | Khandkar et al. |
| 2004/0024461 A1 | 2/2004 | Ferree | | 2008/0082169 A1 | 4/2008 | Gittings et al. |
| 2004/0024462 A1 | 2/2004 | Ferree et al. | | 2009/0018663 A1 | 1/2009 | Cook et al. |
| 2004/0030389 A1 | 2/2004 | Ferree | | | | |
| 2004/0030390 A1 | 2/2004 | Ferree | | | | |
| 2004/0030391 A1 | 2/2004 | Ferree | | | | |
| 2004/0034426 A1 | 2/2004 | Errico et al. | | | | |

FOREIGN PATENT DOCUMENTS

| | | | |
|---|---|---|---|
| FR | 2718635 A1 | * | 10/1995 |
| FR | 2 730 159 A1 | | 8/1996 |
| FR | 2 805 985 A1 | | 9/2001 |
| FR | 2 824 261 A1 | | 11/2002 |
| WO | WO-91/13598 | | 9/1991 |
| WO | WO-94/04100 A1 | | 3/1994 |
| WO | 9509587 | | 4/1995 |
| WO | 9710780 | | 3/1997 |
| WO | 0024342 | | 5/2000 |
| WO | 0101893 | | 1/2001 |
| WO | WO-01/01893 | | 1/2001 |
| WO | WO-03/084449 A1 | | 10/2003 |
| WO | 03090649 | | 11/2003 |
| WO | WO-2004/019828 A1 | | 3/2004 |
| WO | 2004026186 | | 4/2004 |
| WO | WO-2004/026186 A1 | | 4/2004 |

| | | | |
|---|---|---|---|
| 2004/0068318 A1 | 4/2004 | Coates et al. | |
| 2004/0068320 A1 | 4/2004 | Robie et al. | |
| 2004/0073311 A1 | 4/2004 | Ferree | |
| 2004/0117022 A1 | 6/2004 | Marnay et al. | |
| 2004/0133281 A1 | 7/2004 | Khandkar et al. | |
| 2004/0138750 A1 | 7/2004 | Mitchell | |
| 2004/0143270 A1 | 7/2004 | Zucherman et al. | |
| 2004/0143332 A1 | 7/2004 | Krueger et al. | |
| 2004/0148028 A1 | 7/2004 | Ferree et al. | |
| 2004/0167628 A1 | 8/2004 | Foley | |
| 2004/0176772 A1 | 9/2004 | Zubok et al. | |
| 2004/0176773 A1 | 9/2004 | Zubok et al. | |
| 2004/0176774 A1 | 9/2004 | Zubok et al. | |
| 2004/0176777 A1 | 9/2004 | Zubok et al. | |
| 2004/0176778 A1 | 9/2004 | Zubok et al. | |
| 2004/0176843 A1 | 9/2004 | Zubok et al. | |
| 2004/0176852 A1 | 9/2004 | Zubok et al. | |

* cited by examiner

140

140

TWO-COMPONENT ARTIFICIAL DISC REPLACEMENTS

CROSS-REFERENCE TO RELATED APPLICATIONS

This application claims priority from U.S. Provisional Patent Application Ser. No. 60/374,747, filed Apr. 23, 2002; and is a continuation-in-part of U.S. patent application Ser. No. 10/413,028 entitled "Spacerless Artificial Disc Replacements," filed Apr. 14, 2003, the entire content of both applications is incorporated herein by reference.

FIELD OF THE INVENTION

This invention relates generally to artificial disc replacements (ADRs) and total disc replacements (TDRs) and, more particularly, directly articulating replacements based on two components.

BACKGROUND OF THE INVENTION

Many spinal conditions, including degenerative disc disease, can be treated by spinal fusion or artificial disc replacement (ADR). ADR has several advantages over spinal fusion. The most important advantage of ADR is the preservation of spinal motion. Spinal fusion eliminates motion across the fused segments of the spine. Consequently, the discs adjacent to the fused level are subjected to increased stress. The increased stress increases the changes of future surgery to treat the degeneration of the discs adjacent to the fusion. However, motion through an ADR also allows motion through the facet joints. Motion across arthritic facet joints could lead to pain following ADR. Some surgeons believe patients with degenerative disease and arthritis of the facet joints are not candidates for ADR.

Current ADR designs do not attempt to limit the pressure across the facet joints or facet joint motion. Indeed, prior art ADR generally do not restrict motion. For example, some ADR designs place bags of hydrogel into the disc space. Hydrogel bags do not limit motion in any direction. In fact, bags filled with hydrogels may not provide distraction across the disc space. ADR designs with metal plates and polyethylene spacers may restrict translation but they do not limit the other motions mentioned above. The articular surface of the poly spacer is generally convex in all directions. Some ADR designs limit motion translation by attaching the ADR halves at a hinge.

FIG. 1A is a lateral view of a prior-art artificial disc replacement (ADR) 30. FIG. 1B is an anterior view of the prior-art ADR 30. FIG. 1C is a drawing which shows the prior-art ADR 30 in flexion, and FIG. 1D is a drawing which shows the ADR device 30 in extension. Note that, due to impingement, left bending as permitted by the typical prior-art device, increases pressure on the left facet, whereas right bending increases pressure on the right facet. Rotation increases pressure on the right facet and the left facet, and vice versa.

The alignment of one Artificial Disc Replacement (ADR) endplate (EP) relative to the other ADR EP is critical to the function of articulating ADRs. Many ADRs rely on movement between a convexity on one ADR EP and a concavity on the other ADR EP. Alternatively, convex spacers are used between concavities on the ADR EPs. Improperly aligned ADR EPs risk excessive surface wear from incongruent opposing articulating surfaces. Furthermore, improper alignment will decrease ADR motion.

The endplates of prior art ADRs are inserted simultaneously to assure proper alignment. Most ADRs are held in the disc space by the fit of projections from the ADR EP into the vertebra above and below the ADR. Inserting ADR EPs simultaneously limits the length of these projections, however.

SUMMARY OF THE INVENTION

This invention is directed to artificial disc replacements (ADRs) and total disc replacements (TDRs) based upon two, directly articulating components. The result is a restricted motion ADR that better approximates more normal spinal flexion, extension, and lateral bending. In particular, the preferred embodiments should allow at least 10 degrees of movement in the flexion-to-extension direction, and at least 5 degrees of movement in the lateral bending direction.

The preferred embodiment has two components, one with a concave articulating surface, and the other with a convex articulating surface. The radius of curvature of the articulating surface is smaller in the anterior to posterior direction of the ADR than radius of curvature of the articulating surface in the left to right direction of the ADR. The use of an articulating surface with two or more radius of curvature also limits axial rotation, thereby protecting the facet joints and the Annulus Fibrosus (AF). The two different radii used to create the articulating surfaces also naturally leads to an oval shape as seen from the top, which fits the oval shape of the vertebral endplate better than circularly shaped ADRs.

Both components are preferably made of a hard material and are highly polished to reduce friction. For example, either or both components could be made of chrome cobalt, titanium, or other suitable alloys, or a ceramic including alumina, zirconia, calcium phosphate, or other suitable material. The vertebra-contacting surfaces of the ADR may have projections such as keels that penetrate the vertebral endplates, as shown in the Figure. The vertebral surfaces of the components may be treated to promote bone ingrowth. For example, the vertebral surfaces of the components may have plasma spray or beads. Alternatively, one or both components may be cemented directly to the vertebrae, in which case one of the components could be made of polyethylene or other "softer" load-bearing material.

DETAILED DESCRIPTION OF THE INVENTION

The present invention limits both facet joint pressure and facet joint motion. Broadly, the pressure on the facet joints is lowered from the preoperative pressure by distracting the disc space. The present invention also reduces the facet joint pressure by eliminating or significantly reducing motion across the ADR that increase the pressure on the facet joints. Specifically, ADR design in accordance with the various embodiments restricts spinal extension, rotation, translation, and lateral bending. Forward flexion is not restricted as forward flexion decreases the pressure on the facet joints.

Figure 1A:
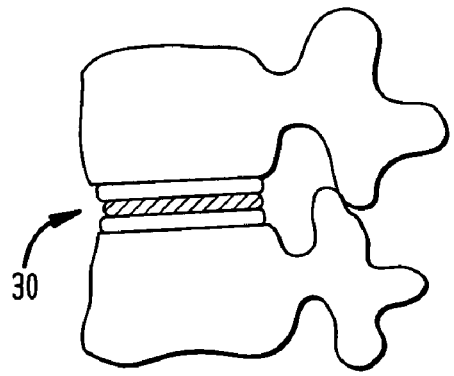
FIG. 1A is a lateral view of a prior art artificial disc replacement (ADR)
Figure 1B:
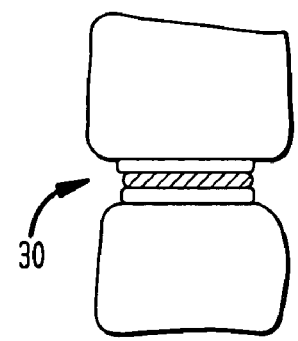
FIG. 1B is an anterior view of the prior art ADR shown in FIG. 1A.
Figure 1C:
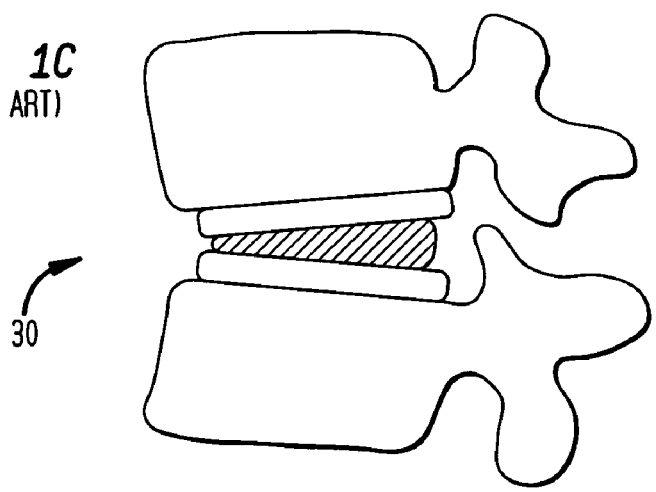
FIG. 1C show the prior art ADR of FIG. 1A in flexion.
Figure 1D:
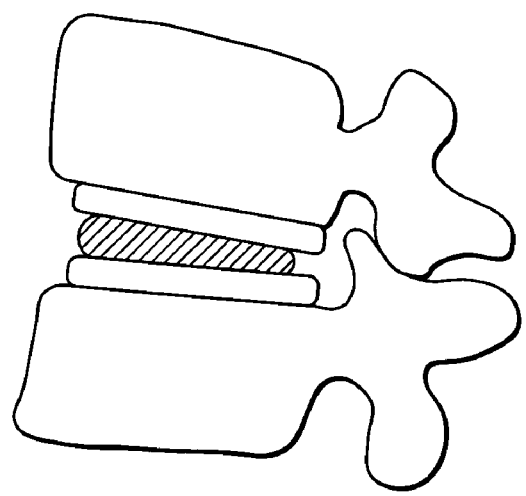
FIG. 1D shows the prior art ADR of FIG. 1A in extension.
Figure 2A:
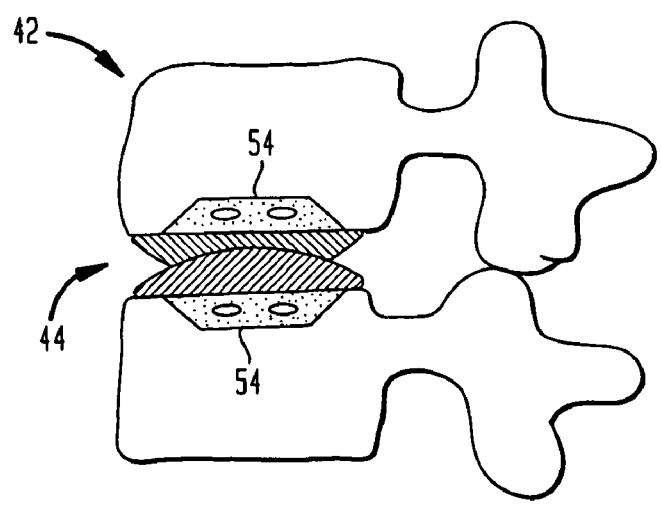
FIG. 2A is a sagittal cross section of the spine and an ADR inserted between two vertebrae of the spine, in accordance with certain preferred embodiments of the present invention.
Figure 2B:
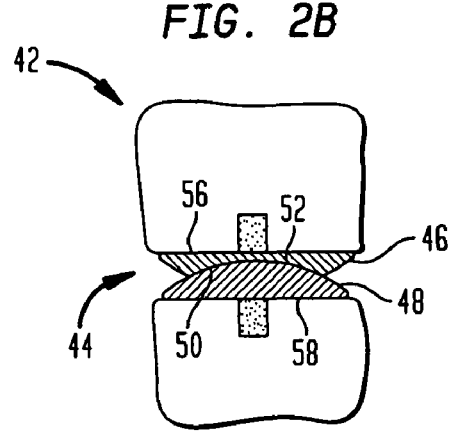
FIG. 2B is a coronal cross section of the spine and the ADR of FIG. 2A.
Figure 2C:
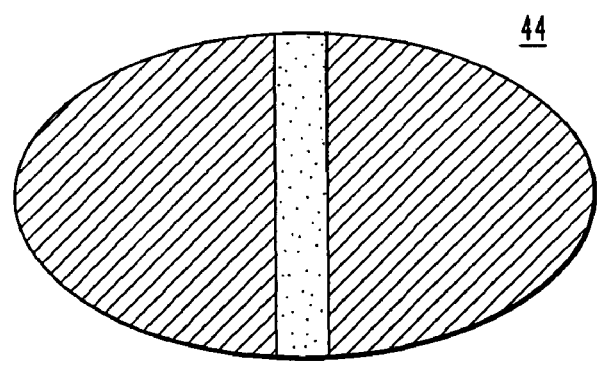
FIG. 2C is a top view of the ADR of FIG. 2A.
Figure 3A:
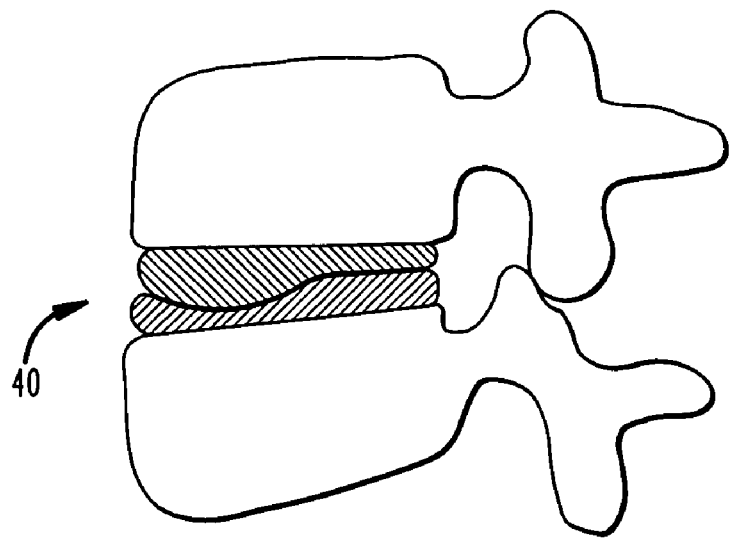
FIG. 3A shows an ADR, in accordance with another preferred embodiment of the present invention.

FIG. 3A is a simplified drawing of a restricted motion artificial disc replacement (ADR) 40 constructed in accordance with this invention. FIG. 2A is a sagittal cross section of the spine 42 and an ADR 44 related to that shown in FIG. 3A. FIG. 2B is a coronal cross section of the spine 42 and the ADR 44 of FIG. 2A. This embodiment has two components 46, 48 one with a concave articulating surface 50, and the other with a convex articulating surface 52. The radius of curvature of the articulating surfaces 50, 52 is smaller in the anterior to posterior direction of the ADR (FIG. 2A) than radius of curvature of the articulating surfaces 50, 52 in the left to right direction of the ADR (FIG. 2B). This design approximates more normal spinal flexion, extension, and lateral bending. That is, the ADR should allows at least 10 degrees of movement in the flexion-to-extension direction, and at least 5 degrees of movement in the lateral bending direction. The use of an articulating surface with two or more radius of curvature limits axial rotation. Limiting axial rotation protects the facet joints and the Annulus Fibrosus (AF).

FIG. 2D is a top view of the ADR 44. The preferred oval shape is caused by the two different radii that create the articulating surfaces. The oval also fits the oval shape of the vertebral endplate better than circularly shaped ADRs. Both components are preferably made of a hard material and are highly polished to reduce friction. For example, either or both components could be made of chrome cobalt, titanium, or other suitable alloys, or a ceramic including alumina, zirconia, calcium phosphate, or other suitable material. The vertebra-contacting surfaces of the ADR may have projections 54 such as keels that penetrate the vertebral endplates, as shown in FIG. 2A. Referring to FIG. 2B, the vertebral surfaces 56, 58 of the respective components 46, 48 may be treated to promote bone ingrowth. For example, the vertebral surfaces of the components may have plasma spray or beads. Alternatively, one or both components may be cemented directly to the vertebrae, in which case one of the components could be made of polyethylene or other "softer" load-bearing material.

Figure 3B:
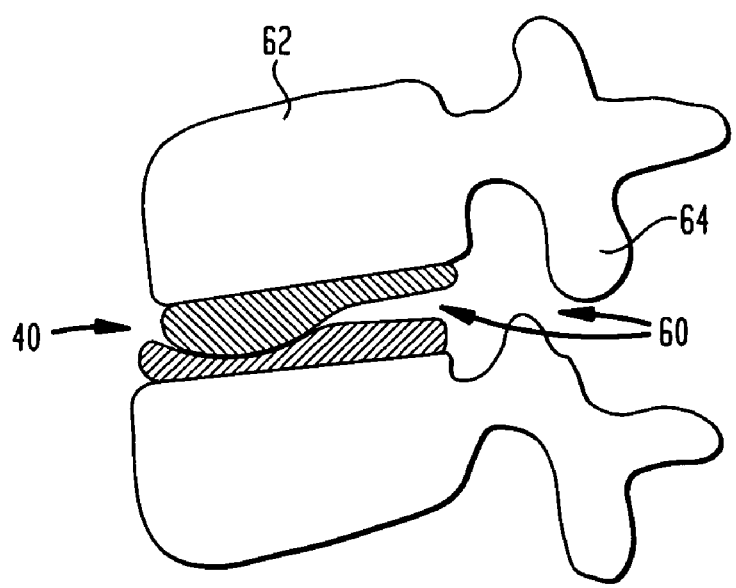
FIG. 3B shows the ADR of FIG. 3A in flexion.
Figure 3C:
FIG. 3C shows the ADR of FIG. 3A in extension.
Figure 3D:
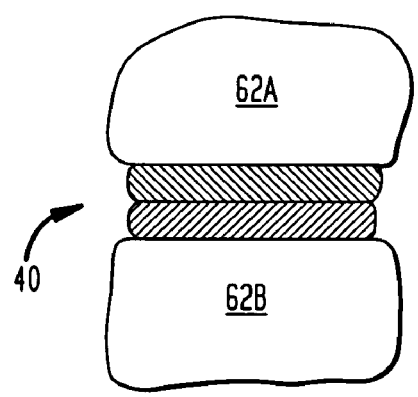
FIG. 3D is an anterior view of the ADR of FIG. 3A attached to adjacent vertebrae.
Figure 3E:
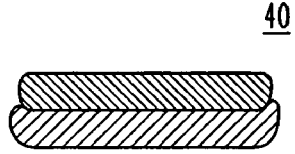
FIG. 3E shows a drawing of the embodiment of FIG. 3A illustrating how lateral bending is limited by contact on the left when bending is to the left, and on the right when bending is to the right.
Figure 3F:
FIG. 3F shows a lateral view of the restricted motion ADR shown in FIG. 3E.

FIG. 3B is a drawing of the ADR device 40 of FIG. 3A in flexion, illustrating the way in which gaps 60 are created in the posterior of the vertebrae 62 and the facet joint 64. FIG. 3C is a drawing of the ADR device 40 of FIG. 3A in extension, showing how posterior contact is limited. FIG. 3D is an anterior view of the ADR 40 of FIG. 3A attached to adjacent vertebrae 62A, 62B. FIG. 3E is a drawing of the ADR 40 of FIG. 3E illustrating how lateral bending is limited by contact on the left when bending is to the left, and on the right when bending is to the right. FIG. 3F is a lateral view of the restricted motion ADR 40 according to the invention, illustrating how rotation and translocation are limited by a spoon-on-spoon cooperation.

Figure 4:
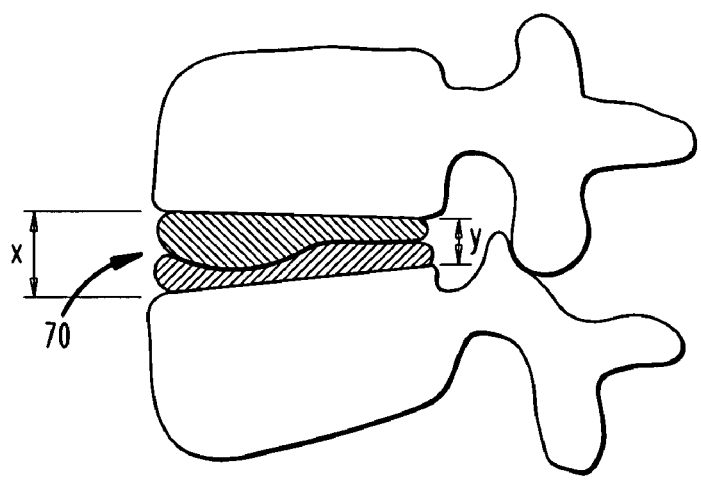
FIG. 4 shows an ADR in accordance with another preferred embodiment of the invention.
Figure 5:
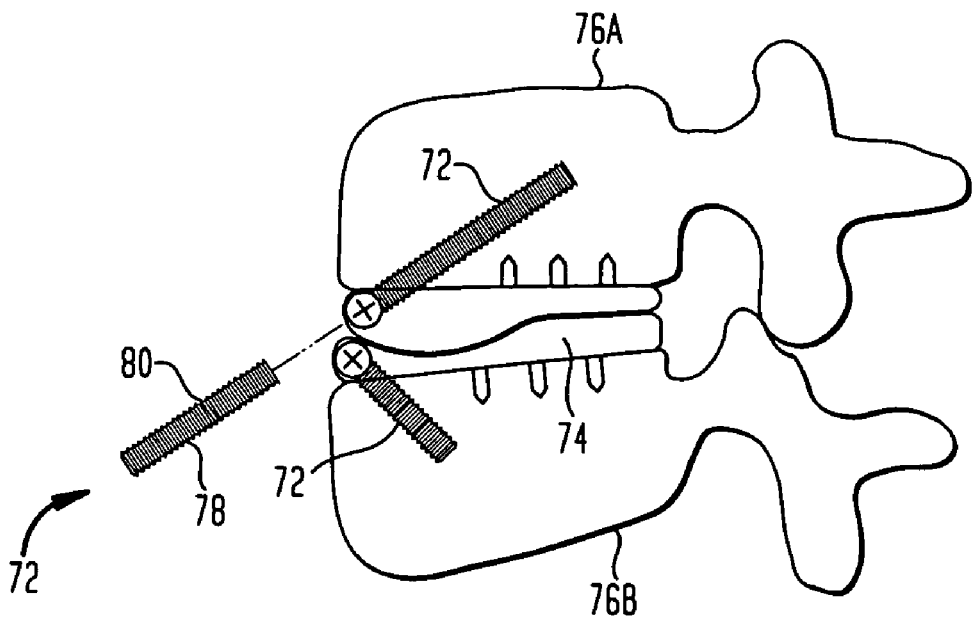
FIG. 5 shows an ADR in accordance with another preferred embodiment of the present invention.
Figure 6:
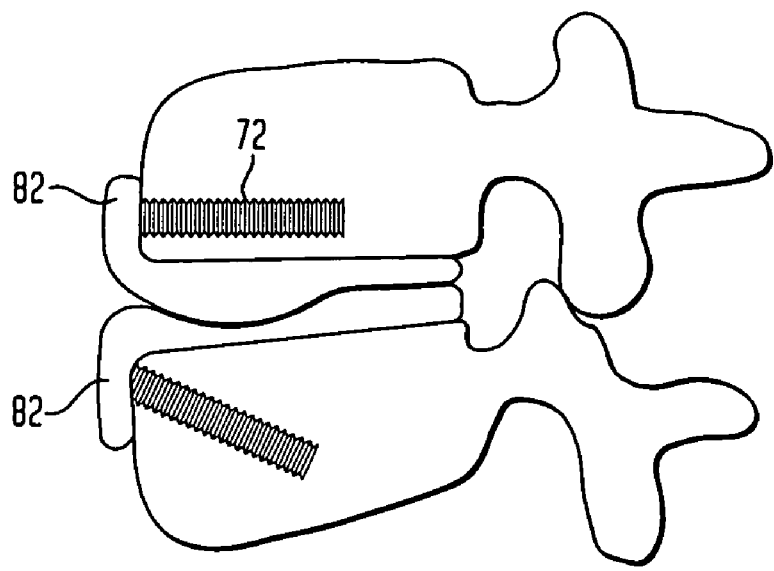
FIG. 6 shows an ADR having attachment flanges, in accordance with still another preferred embodiment of the present invention.

FIG. 4 is a drawing of an ADR 70, in accordance with another preferred embodiment of the invention, illustrating how a wedge or trapezoid-shaped ADR may be used according to the invention to preserve lordosis. FIG. 5 is a side-view drawing which illustrates a way in which screws 70 may be used to fix an ADR 74 according to the invention to upper and lower vertebrae 76A, 76B. In particular, a fastener 70 may be used having coarse threads 78 received by the bone, and finer threads 80 associated with actually locking the ADR into place. FIG. 6 is a drawing which shows the use of anterior flanges 82 facilitating the use of generally transverse, as opposed to diagonally oriented, screws 72.

Figure 7A:
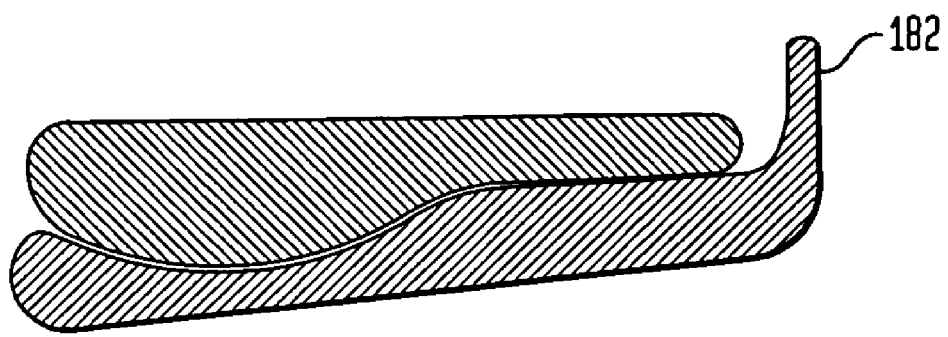
FIG. 7A is a side-view drawing of an ADR, in accordance with a further alternative embodiment according to the invention.
Figure 7B:
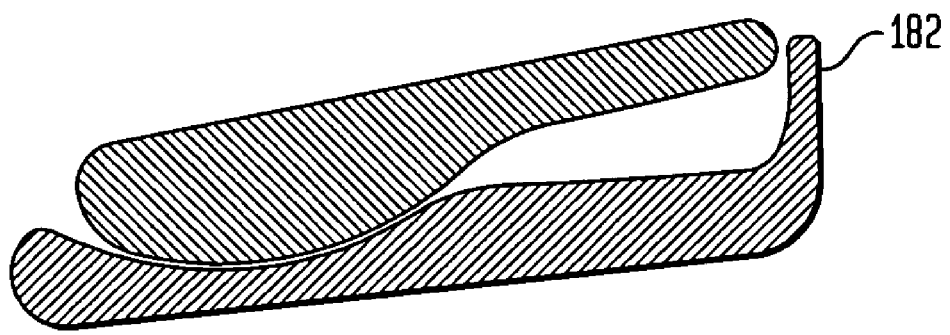
FIG. 7B shows the ADR of FIG. 7A in flexion.
Figure 8:
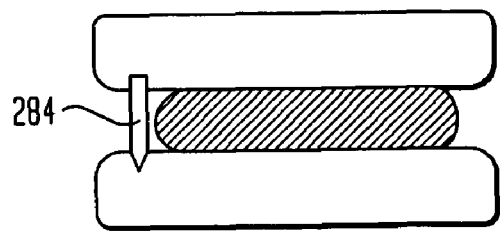
FIG. 8 is a side-view drawing showing an ADR having an anterior check rein to prevent extension, in accordance with still further preferred embodiments of the present invention.
Figure 9:
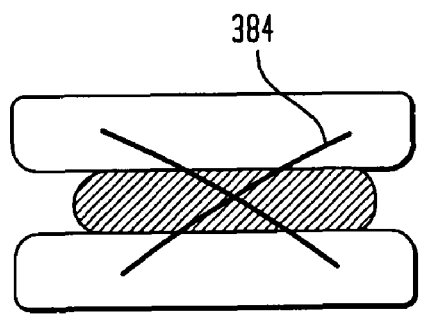
FIG. 9 shows an ADR having cross-coupled check reins, in accordance with other preferred embodiments of the present invention.
Figure 10:
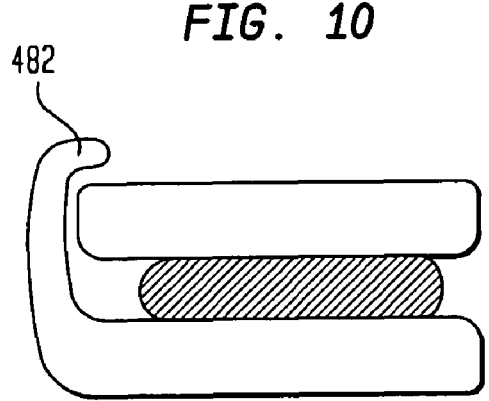
FIG. 10 shows an ADR having an anterior flange configured to inhibit extension, in accordance with yet further preferred embodiments of the present invention.

FIG. 7A is a side-view drawing of an ADR 140 in accordance with another preferred embodiment of the invention, featuring an optional lip 182 to prevent the trapping of soft tissue during the movement from a flexion to neutral position. FIG. 7B shows the flange device 182 of FIG. 7A in flexion. As a substitute for, or in conjunction with, peripheral flanges, check reins may be used to restrict motion. FIG. 8 is a side-view drawing showing the use of an anterior check rein 284 to prevent extension, for example. Lateral check reins may be used to prevent lateral bending, and cross-coupled check reins may be used to prevent translation. FIG. 9 depicts the use of cross-coupled check reins 384. FIG. 10 illustrates the optional use of an anterior flange 482 configured to inhibit extension.

Figure 11A:
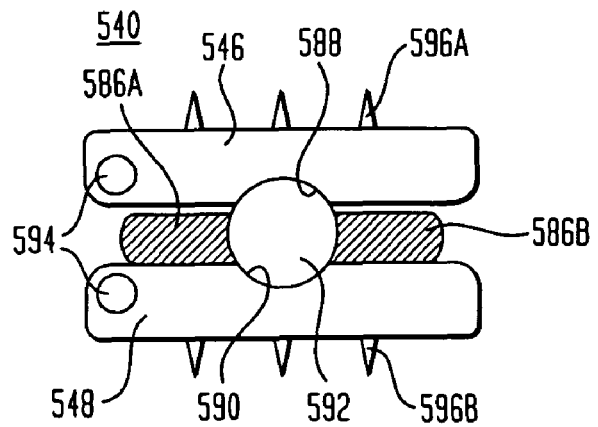
FIG. 11A is a drawing which shows an ADR, in accordance with still another preferred embodiment of the invention.
Figure 11B:
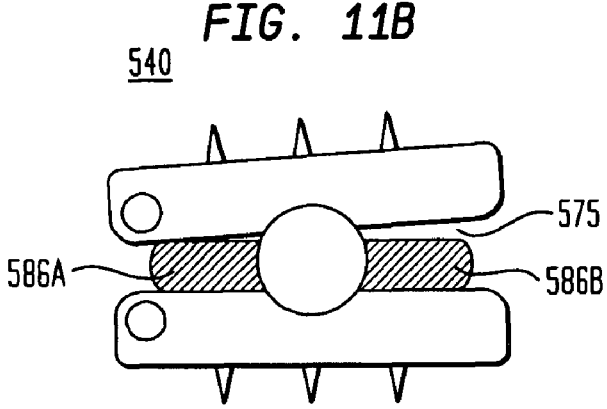
FIG. 11B is a drawing which shows the device of FIG. 11A in flexion.
Figure 11C:
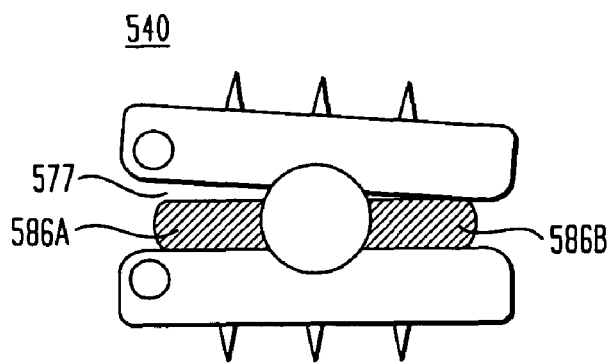
FIG. 11C is a drawing which shows the device of FIG. 11A in extension.
Figure 11D:
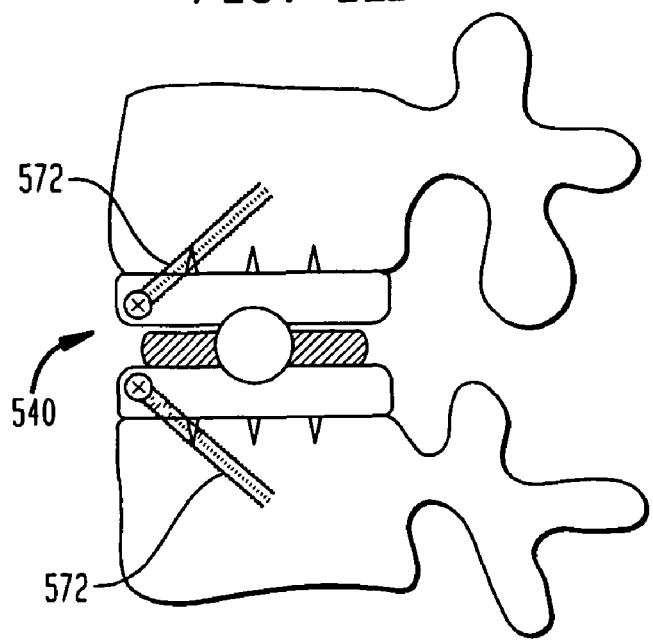
FIG. 11D shows a side view of the ADR of FIG. 11A being held in place using screws.
Figure 11E:
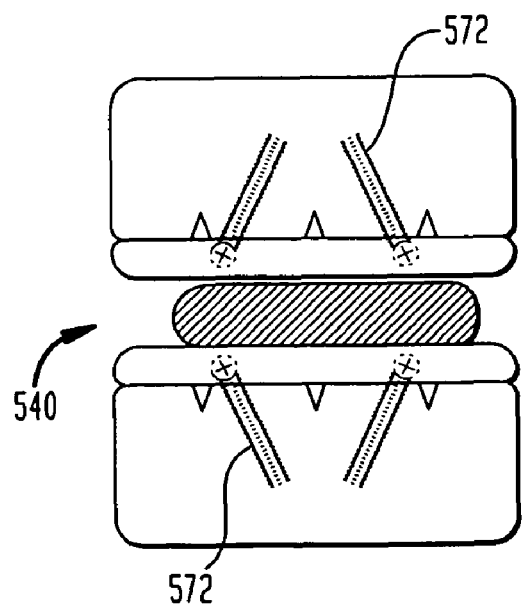
FIG. 11E shows a posterior view of the ADR of FIG. 11D.

FIG. 11A is a drawing which illustrates yet a different embodiment of the invention, including an ADR 540 having flexion and/or extension blocks 586A, 586B. Shown in FIG. 11A, endplates 546, 548, preferably metal, include respective recesses 588, 590 to receive a centralized rod 592, also preferably metallic. On either side of the rod, but between the end plates, there is disposed a more wearing bearing block of material 586 such as polyethylene, one preferably associated with flexion and an opposing block associated with extension. Holes 594 may be provided for fixation along with projections 596A, 596B for enhanced adherence. FIG. 11B is a drawing which shows the ADR device 540 of FIG. 11A in flexion, and FIG. 11C shows the ADR device 540 in extension. Note that, during flexion (FIG. 11B), a posterior gap 575 is created, whereas, in extension (FIG. 11C), an anterior gap 577 is created. In this embodiment, the degree of flexion and extension may be determined by the thickness of the flexion/extension blocks 586A, 586B, which may determined at the time of surgery. FIG. 11D is a side-view drawing of the way in which screws 572 may be used to hold the ADR device 540 of FIG. 11A in place. FIG. 11E an A-P view of the ADR 540 of FIG. 11A. Note that the screws 572 may converge or diverge, to increase resistance to pull-out.

Figure 12:
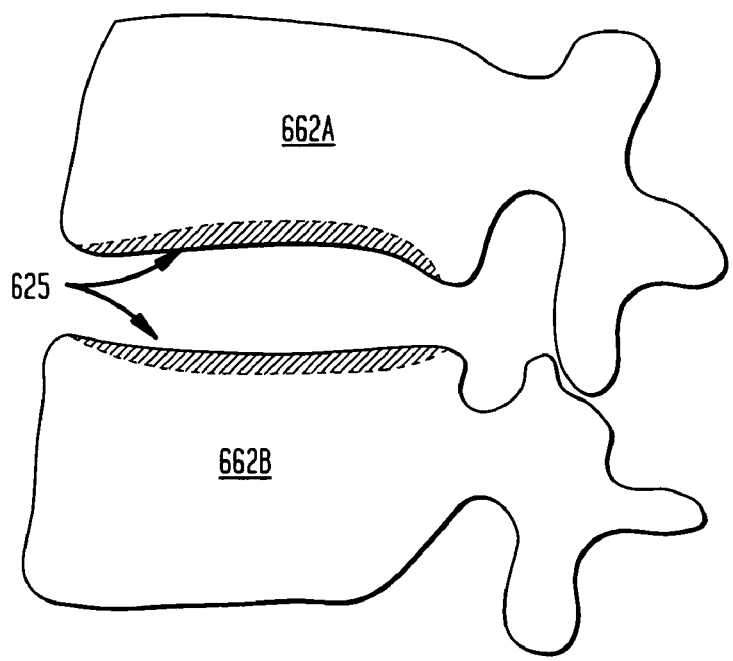
FIG. 12 is a side-view drawing of a disc space between two vertebrae.

The superior surface of the superior endplate and the inferior surface of the inferior endplate of the ADR could be convex. The convex surfaces of the ADR would fit the concavities of the endplates of the vertebrae. The endplates could be decorticated to promote bone ingrowth into the endplates of the ADR. An expandable reamer or a convex reamer could preserve or increase the concavities. The concavities have two important advantages. First, they help prevent migration of the ADR. The convexities of the ADR fit into the concavities of the vertebrae. Second, the majority of support for the ADR occurs at the periphery of the vertebral endplates. Thus, reaming away a portion of the central, concave, portion of the vertebrae promotes bone ingrowth through exposure to the cancellous interior of the vertebrae, yet preserves the stronger periphery. FIG. 12 is a side-view drawing which shows the area 625 that could be removed to customize the vertebrae 662A, 662B so as to fit an ADR (not shown) according to the invention and/or promote ingrowth.

Figure 13:
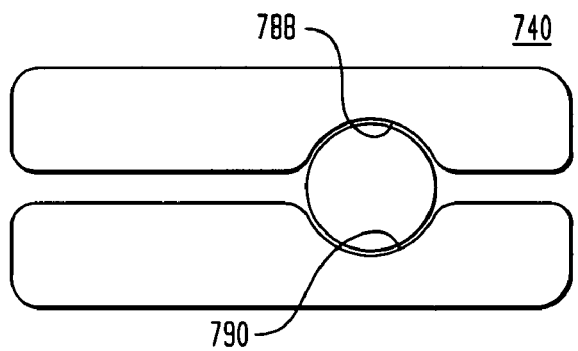
FIG. 13 shows an ADR, in accordance with still further preferred embodiments of the present invention.
Figure 14:
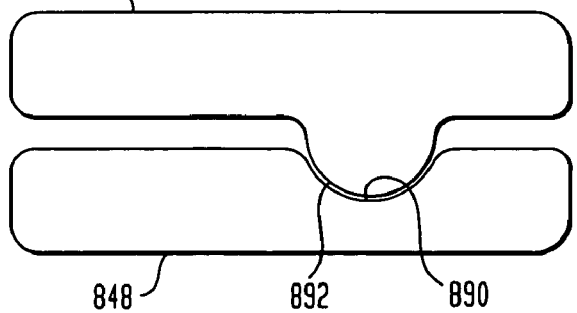
FIG. 14 shows an ADR, in accordance with yet further preferred embodiments of the present invention.

The endplates of the ADR could be any material that promotes bone ingrowth. For example, titanium or chrome-cobalt with a porous, beaded, or plasma spray surface. The flexion and extension blocks would likely be made of polyethylene, but could also be made of other polymers, ceramic, or metal. The central rod or axle would likely made of the same metal as the endplates of the ADR, but could also be made of polyethylene or other polymer, or ceramic. A metal or ceramic rod would have better surface wear than a polyethylene rod. A limited amount of compression to axial loads could occur when a portion of the ADR endplates lie against the polyethylene blocks. A central rod is preferred over incorporating a raised rod like projection into one of the endplates. The central rod allows rotation about twice as much surface area (the superior and inferior surfaces). The increased surface area decreases the pressure on the surface during rotation about the central axle/rod. FIG. 13 shows an ADR 740, in accordance with another preferred embodiment of the present invention having rotation surfaces 788, 790. FIG. 14 is a side-view drawing of an ADR 840 which shows a partial rotation surface 892 on a first endplate 846 that is received by a concavity 890 in an opposing endplate 848. Both versions shown in FIGS. 13 and 14 are assembled within the disc space.

Figure 15A:
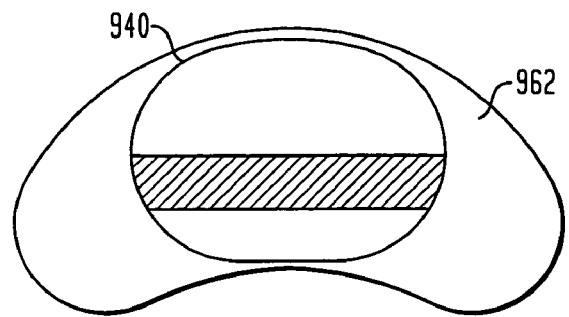
FIG. 15A shows a top plan view of the ADR of FIG. 13 positioned between vertebrae.
Figure 15B:
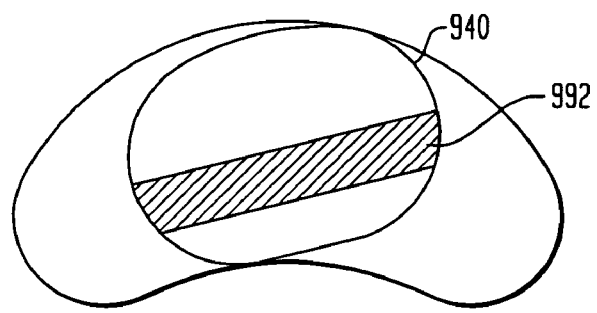
FIG. 15B shows another top plan view of the ADR of FIG. 13 positioned between vertebrae.

Alignment of the ADR is critical. If the central rod or axle is diagonal to the long axis of the vertebral endplate, the patient will bend to the left or right while bending forward. Novel (for and ADR) alignment guides are described below. Furthermore, if the axle is made of polyethylene, metallic markers will be incorporated into the ends of the axle. Surgeons can assure proper alignment by fluoroscopic images during surgery. FIG. 15A is a end-view of an ADR 940 according to the invention placed on the vertebrae 962 seen from a top-down A-P view. FIG. 15B is a drawing of the embodiment of FIG. 15A with the ADR 940 and axle 992 rotated. Should the patient have trouble bending forward, and so forth, the patient may twist at the side while bending forward, as appropriate.

Figure 16:
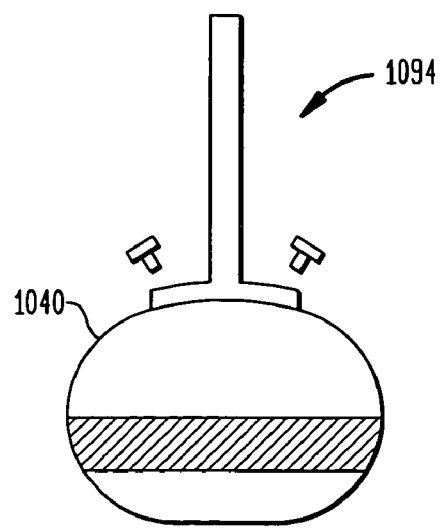
FIG. 16 shows a removable alignment guide used for placement of an ADR, in accordance with certain preferred embodiments of the present invention.
Figure 17:
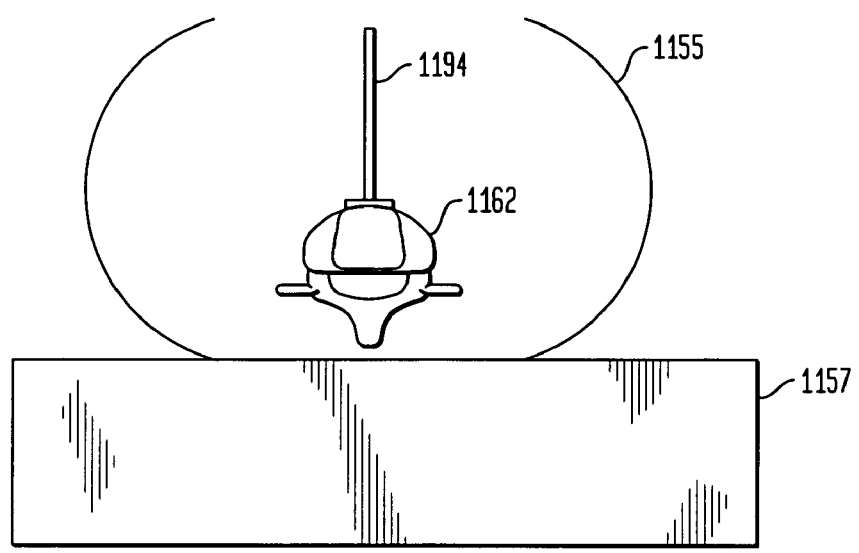
FIG. 17 is a simplified cross-sectional view of a patient on an operating table, showing the alignment guide being coupled with an ADR for inserting the ADR into the patient.
Figure 18A:
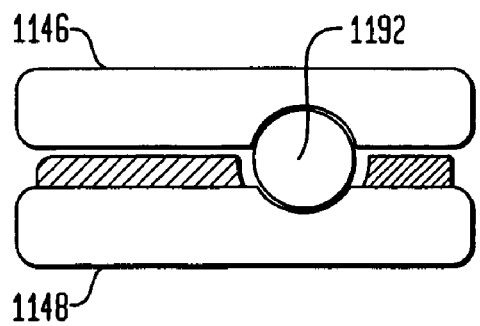
FIG. 18A shows an ADR, in accordance with another preferred embodiment of the present invention.

FIG. 16 is a drawing which shows a removable alignment guide 1094 used for placement of the ADR 1040. FIG. 17 is a simplified cross-sectional view of a patient 1155 on an operating table 1157, showing the alignment guide 1194 in position. In particular, the alignment guide 1194 is preferably perpendicular to the table 1157, the patient 1155, and vertebrae 1162 with respect to al proper orientation. FIG. 18A is a lateral view using fluoroscopy which shows the circular cross-section of the axle 1192 when properly aligned.

Figure 18B:
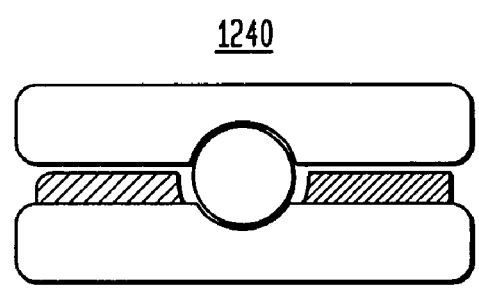
FIG. 18B shows an ADR, in accordance with another preferred embodiment of the present invention.
Figure 18C:
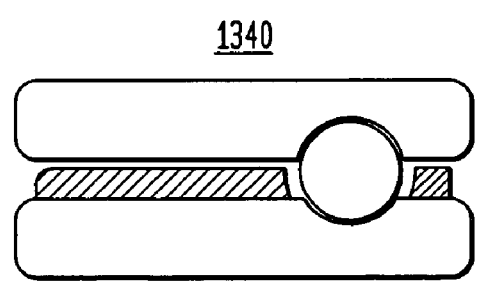
FIG. 18C shows an ADR, in accordance with still another preferred embodiment of the present invention.

The ADR endplates 1146, 1148 could be designed to locate the axle 1192 transversely in any location from anterior to posterior. The location of the axle 1192 may vary depending on the disc that will be replaced. For example, the axle may located at the junction of the anterior $2/3$rd and posterior $1/3^{rd}$ for the L5/S1 disc (FIG. 18A) but at the anterior $1/2$ and posterior $1/2$ for the L3/L4 disc (FIG. 18B). Similarly, the degree of wedge shape will vary with the disc to be replaced. L5/S1 will require a more wedge shaped ADR than L3/L4. FIG. 18B is an anterior view of an ADR 1240, in accordance with still another preferred embodiment of the present invention, and FIG. 18C is an anterior view of an ADR 1340 in accordance with another preferred embodiment of the present invention.

Preoperative templates will be provided to help the surgeon predict which ADR will be needed. The ADR could be inserted fully assembled or constructed in the disc space. Construction within the disc space allows the surgeon to force spikes of the ADR endplate into the vertebrae. Assembly in the disc space also allows maximum use of the vertebral concavities. The polyethylene blocks contain features to allow them to snap into place. Polyethylene trays with "snap" features are well described in the total knee replacement literature.

FIGS. 19A-19I illustrate steps associated with installing a restricted motion ADR according to the invention. In the preferred embodiment the ADR relies on bone ingrowth. Alternatively, the ADR may be cemented to the vertebrae using, for example, methyl methacrylate. Novel, safer cutting guides, and a novel distraction instruments are described. The system also provides trial implants and instruments to determine the balance and tension of the surrounding soft tissues.

Figure 19A:
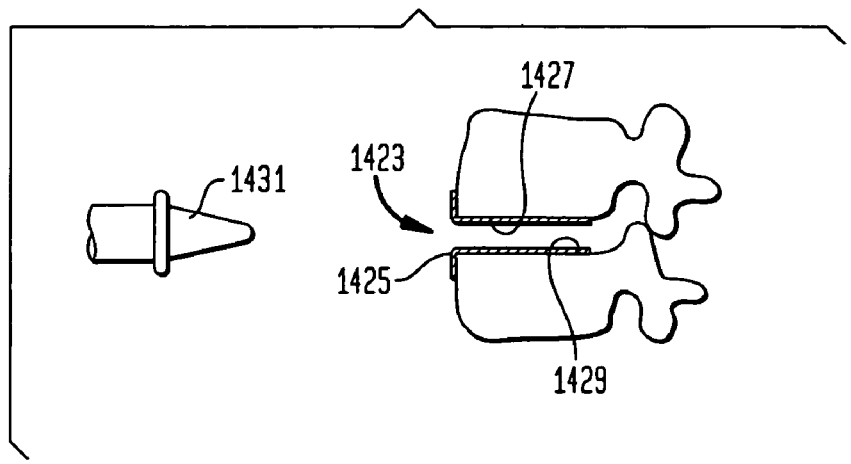
FIGS. 19A-19I show a method of inserting an ADR, in accordance with certain preferred embodiments of the present invention.
Figure 19B:
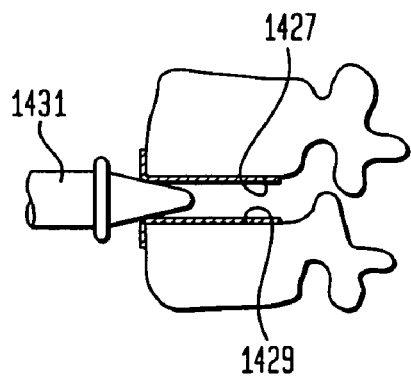
Figure 19C:
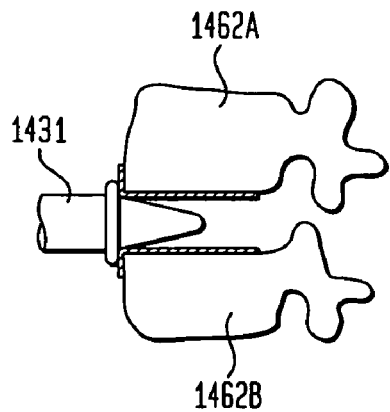

As an initial step, a portion of the disc annulus and most or all of the disc nucleus are removed (not shown). As a second step, the disc space 1423 is distracted, as shown in FIG. 19A. In this case a novel implant sleeve 1425 is used to protect the end plates 1427, 1429, and an impact serial distracter 1431 is used between these sleeves 1423, 1425. FIG. 19B shows the impact distraction element 1431 in place between the end plates 1427, 1429, and FIG. 19C shows the tool 1431 being manipulated to spread the vertebrae apart 1462A, 1462B.

Figure 19D:
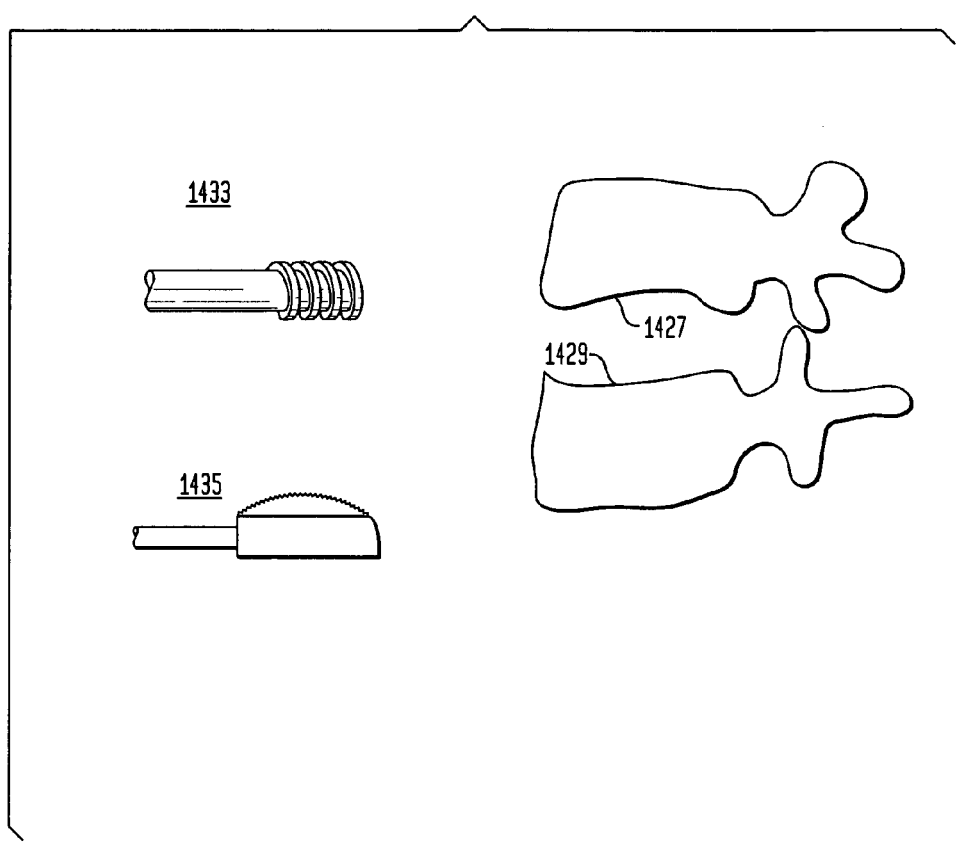
Figure 19E:
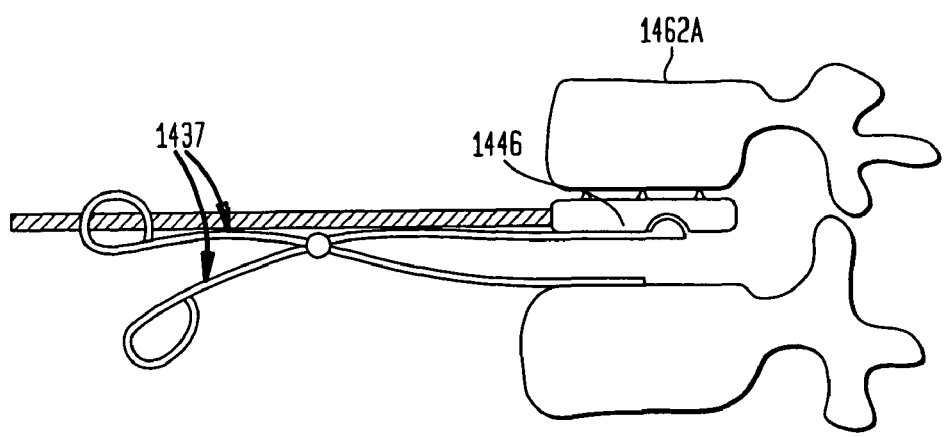

According to a third step, the end plates 1427, 1429 are prepared through the use of a reamer 1433 and/or circular grinder 1435 with the distraction sleeves removed, as shown in FIG. 19D. As a fourth step, the trial ADR is inserted (not shown) so as to select a proper size ADR (step 5, also not shown). Having determined the proper size, a first end plate 1446 for the final ADR is inserted as shown in FIG. 19E with a tool 1437 used to force the end plate of the ADR into the vertebrae 1462, whether upper or lower.

Figure 19F:
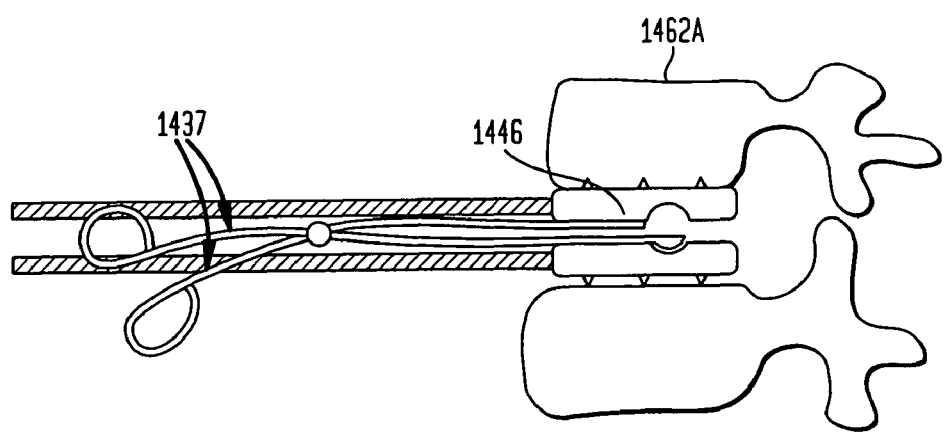
Figure 19G:
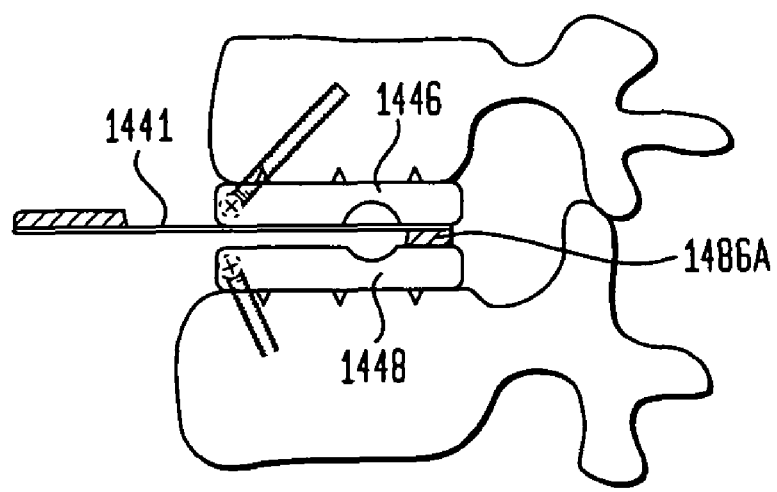

This section of the disclosure emphasizes methods and instruments that allow for the separate insertion of ADR EPs. Aligning the insertion of a second ADR EP relative to a first EP that enables the use of longer projections from the ADR EPs, resulting in a more controlled procedure. Referring to FIGS. 19E and 19F in particular, the upper ADR EP 1446 has been press fit into the vertebra 1462A above the disc space. A special tool 1439 fits into a portion of the ADR EP 1446 that was inserted first, thereby aligning the insertion of the second ADR EP 1448. The tool 1439 can also be used to press the second ADR EP 1448 into the vertebra. Although FIGS. 19E and 19F illustrate the use of an instrument that fits into cylinder-like concavities, the instrument could fit into other shapes in the ADR EPs, including slots and other shapes with flat sides.

In FIG. 19F, the second end plate 1448 is inserted, such that the opposing end plates 1446, 1448 are flush with one another. The tool 1439 used for this purpose forces the second plate 1448 of the ADR into the second vertebrae 1462B while simultaneously aligning the concavities 1488, 1490 to receive the axle. Alignment guides may be used in parallel/superimposed fashion to ensure that the opposing end plates 1446, 1448 are oriented properly. In addition, the enlarged ends of the distraction tool may include end features which fit into the cavities for axle, again, to ensure proper orientation. In step 8, shown in FIG. 19G, the end plates 1446, 1448 are optionally screwed into place, and a first poly block 1486A is installed posteriorly using a tool 1441 to snap the block 1486A into position. Note that the posterior poly block may also be preassembled to the inferior ADR end plate 1448, as an option.

Figure 19H:
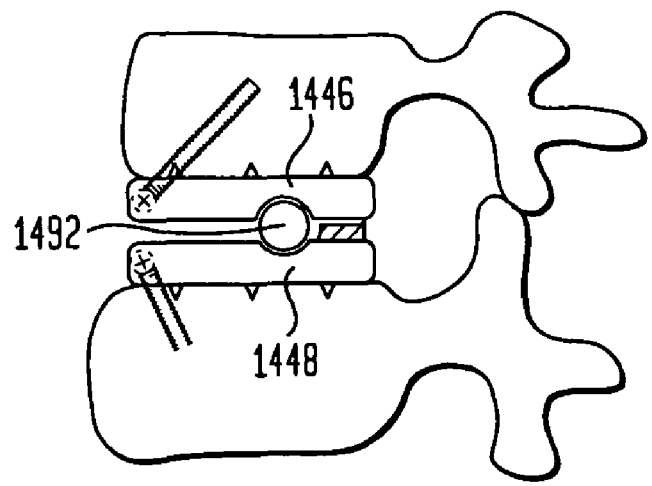
Figure 19I:
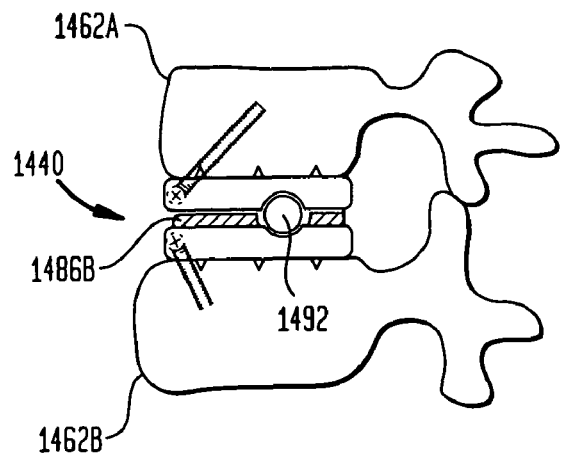
Figure 20:
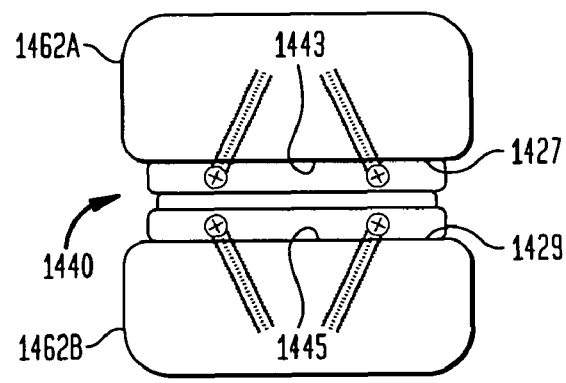
FIG. 20 is an anterior view of the ADR of FIG. 19I installed between opposing vertebrae.
Figure 21:
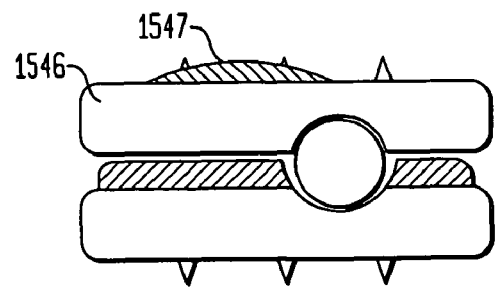
FIG. 21 shows an ADR, in accordance with still further preferred embodiments of the present invention.

FIG. 19H shows the step of inserting an axle 1492 between the end plates 1446, 1448. In step 10, shown in FIG. 19I, the anterior poly block 1486B is snapped in position on the other side of the installed axle 1492. The ADR 1440 could be placed into recessed areas of the vertebrae 1462A, 1462B to help hold it in place. FIG. 20 is an anterior view of the ADR 1440 installed between opposing vertebrae 1462A, 1462B also showing the relative positioning of recesses 1443, 1445 formed in the end plates 1427, 1429 of the vertebrae 1462. FIG. 21 shows the use of optional wedges or convex pieces 1547 attached to the ADR end plate 1546 so as to customize the prosthesis to a particular patient anatomy.

Figure 22:
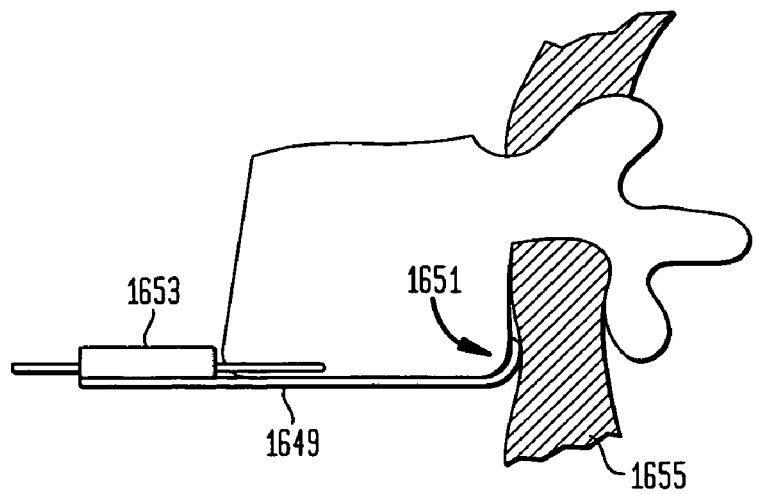
FIG. 22 is a drawing which shows an inventive cutting guide having a curved end to prevent a saw from cutting into the nerves, in accordance with yet further preferred embodiments of the present invention.
Figure 23A:
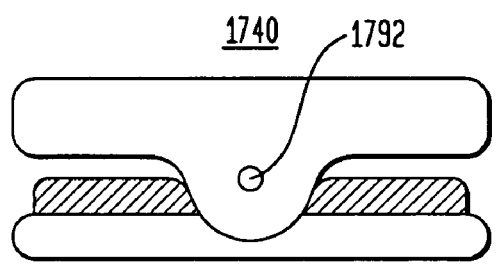
FIG. 23A is a side-view of an ADR having a hinged axle, in accordance with certain preferred embodiments of the present invention.
Figure 23B:
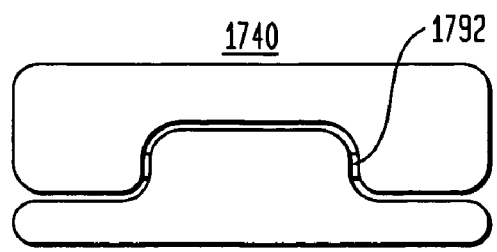
FIG. 23B is an end view of the ADR of FIG. 23A shown without flexion/extension blocks to better illustrate the hinged axle.

FIG. 22 is a drawing which shows an inventive cutting guide 1649 having a curved end 1651 to prevent a saw 1653 from cutting into the nerves 1655. FIG. 23A is a side-view drawing of a further, different embodiment of the invention including an ADR 1740 utilizing a hinged axle 1792. FIG. 23B is an end view of the ADR 1740 of FIG. 23A shown without flexion/extension blocks to better illustrate the hinged portion 1792.

The invention claimed is:

1. An artificial disc replacement (ADR) comprising:
a first monolithic component having a first bone engaging surface and a first inward facing surface including a first articulating surface;
a second monolithic component having a second bone engaging surface and a second inward facing surface including a second articulating surface in contact with the first articulating surface for enabling the first and second components to move relative to one another, wherein the entirety of one of the first or second inward facing surfaces is an articulating surface;
the first component having a first axis extending between leading and trailing ends thereof and a second axis, substantially perpendicular to the first axis, extending between lateral ends of the first component;
the first articulating surface comprising a first arc extending in a first plane substantially parallel to the first axis, the first arc defining a single, continuous arc the entirety of which is centered between equal portions at or near the leading and trailing ends of the first component, and a second arc extending in a second plane substantially parallel to the second axis, the second arc defining a single, continuous arc the entirety of which is centered between equal portions at or near the lateral ends of the first component, wherein the first and second arcs are perpendicular to one another,
wherein the first arc has a radius of curvature which is smaller than a radius of curvature of the second arc.

2. The ADR of claim 1, wherein the first arc defines a concave surface.

3. The ADR of claim 1, wherein the first and second components are constructed from a hard metal, ceramic, or alloys thereof.

4. The ADR of claim 1, wherein the first component is constructed from a hard metal, ceramic, or alloys thereof, and the second component is constructed from a polymer.

5. The ADR of claim 4, wherein the polymer is polyethylene.

6. The ADR of claim 4, wherein the second component is cemented directly to a vertebral body.

7. The ADR of claim 1, wherein the first articulating surface comprises a first convex arc extending between the leading and trailing ends of the first component and a second convex arc extending between the lateral ends of the first component such that the entirety of the first inwardly facing surface is the first articulating surface.

8. The ADR of claim 1, further comprising:
the second component having a third axis extending between leading and trailing ends thereof and a fourth axis, substantially perpendicular to the third axis, extending between lateral ends of the second component;

the second articulating surface comprising a third arc extending in a third plane substantially parallel to the third axis of the second component and a fourth arc extending in a fourth plane substantially parallel to the fourth axis of the second component, the third arc of the second component defining a single, continuous arc the entirety of which is centered between equal portions at or near the leading and trailing ends of the second component and the fourth arc of the second component defining a single, continuous arc the entirety of which is centered between equal portions at or near the lateral ends of the second component, wherein the third and fourth arcs are perpendicular to one another.

9. The ADR of claim 8, wherein the third arc has a radius of curvature which is smaller than a radius of curvature of the fourth arc.

10. The ADR of claim 9, wherein the third arc of the second component defines a convex surface.

11. The ADR of claim 9, wherein the third arc of the second component defines a third concave arc extending between the leading and trailing ends of the second component and the fourth arc of the second component defines a fourth concave arc extending between the lateral ends of the second component.

12. An artificial disc replacement (ADR) comprising:
a first monolithic component having a first bone engaging surface and a first inward facing surface including a first articulating surface;
a second monolithic component having a second bone engaging surface and a second inward facing surface including a second articulating surface in contact with the first articulating surface for enabling the first and second components to move relative to one another, wherein the entirety of one of the first or second inward facing surfaces is an articulating surface;
the first component having a first axis extending between leading and trailing ends thereof and a second axis, substantially perpendicular to the first axis, extending between lateral ends of the first component;
the first articulating surface comprising a first arc extending in a first plane substantially parallel to the first axis and a second arc extending in a second plane substantially parallel to the second axis, wherein the first arc has a radius of curvature which is smaller than a radius of curvature of the second arc, wherein the first arc defines a first continuous arc the entirety of which is centered between equal portions at or near the leading and trailing ends of the first component and the second arc defines a second continuous arc the entirety of which is centered between equal portions at or near the lateral ends of the first component, wherein the first and second arcs are perpendicular to one another.

13. The ADR of claim 12, wherein the first arc defines a continuous concave arc extending between the leading and trailing ends of the first component.

14. The ADR of claim 12, wherein the second arc defines a single, continuous convex arc extending between the lateral ends of the first component.

15. The ADR of claim 12, further comprising:
the second component having a third axis extending between leading and trailing ends thereof and a fourth axis, substantially perpendicular to the third axis, extending between lateral ends of the second component;
the second articulating surface comprising a third arc extending in a third plane substantially parallel to the third axis of the second component and a fourth arc extending in a fourth plane substantially parallel to the fourth axis of the second component, wherein the third arc of the second component defines a single, continuous arc the entirety of which is centered between equal portions at or near the leading and trailing ends of the second component and the fourth arc of the second component defines a single, continuous arc the entirety of which is centered between equal portions at or near the lateral ends of the second component, wherein the third and fourth arcs are perpendicular to one another.

16. The ADR of claim 15, wherein the third arc has a radius of curvature which is smaller than a radius of curvature of the fourth arc.

17. The ADR of claim 15, wherein the third arc of the second component defines a continuous convex arc extending between the leading and trailing ends of the second component.

18. The ADR of claim 17, wherein the fourth arc of the second component defines a continuous convex arc extending between the lateral ends of the second component.

19. An artificial disc replacement (ADR) comprising:
a first monolithic component having a first bone engaging means and a first inward facing surface including a first articulating means;
a second monolithic component having a second bone engaging means and a second inward facing surface including a second articulating means in contact with the first articulating means, wherein the entirety of one of the first or second inward facing surfaces is an articulating surface;
the first articulating means having a first axis extending between leading and trailing ends thereof and a second axis, substantially perpendicular to the first axis, extending between lateral ends thereof;
the first articulating means comprising a first arc extending in a first plane substantially parallel to the first axis and a second arc extending in a second plane substantially parallel to the second axis, wherein the first arc has a radius of curvature is smaller than a radius of curvature of the second arc, and wherein the first arc defines a first concave arc the entirety of which is centered between equal portions at or near the leading and trailing ends thereof and the second arc defines a second continuous concave arc between equal portions at or near the lateral ends thereof.

20. The ADR of claim 19, further comprising:
the second articulating means having a third axis extending between leading and trailing ends thereof and a fourth axis, substantially perpendicular to the third axis, extending between lateral ends thereof;
the second articulating means comprising a third arc extending in a third plane substantially parallel to the third axis of the second articulating means and a fourth arc extending in a fourth plane substantially parallel to the fourth axis of the second articulating means, wherein the third arc has a radius of curvature which is smaller than a radius of curvature of the fourth arc, and wherein the third arc of the second articulating means defines a third convex arc the entirety of which is centered between the leading and trailing ends of the second component and the fourth arc of the second articulating means defines a fourth continuous convex arc the entirety of which is centered between the lateral ends of the second component.

* * * * *

UNITED STATES PATENT AND TRADEMARK OFFICE
CERTIFICATE OF CORRECTION

| | | |
|---|---|---|
| PATENT NO. | : 8,038,713 B2 | Page 1 of 1 |
| APPLICATION NO. | : 10/421304 | |
| DATED | : October 18, 2011 | |
| INVENTOR(S) | : Bret A. Ferree | |

It is certified that error appears in the above-identified patent and that said Letters Patent is hereby corrected as shown below:

Column 10, line 40, before "is" insert --which--.

Signed and Sealed this
Fifteenth Day of January, 2013

David J. Kappos
*Director of the United States Patent and Trademark Office*